(12) United States Patent
Sugimoto et al.

(10) Patent No.: US 11,406,621 B2
(45) Date of Patent: Aug. 9, 2022

(54) PHARMACEUTICAL COMPOSITION

(71) Applicant: KOWA COMPANY, LTD., Nagoya (JP)

(72) Inventors: Shin Sugimoto, Fuji (JP); Akito Minamizono, Fuji (JP)

(73) Assignee: KOWA COMPANY, LTD., Nagoya (JP)

(*) Notice: Subject to any disclaimer, the term of this patent is extended or adjusted under 35 U.S.C. 154(b) by 248 days.

(21) Appl. No.: 16/627,141

(22) PCT Filed: Jun. 29, 2018

(86) PCT No.: PCT/JP2018/024884
§ 371 (c)(1),
(2) Date: Dec. 27, 2019

(87) PCT Pub. No.: WO2019/004449
PCT Pub. Date: Jan. 3, 2019

(65) Prior Publication Data
US 2020/0155514 A1 May 21, 2020

(30) Foreign Application Priority Data
Jun. 30, 2017 (JP) .............. JP2017-128695

(51) Int. Cl.
*A61K 31/423* (2006.01)
*A61K 47/26* (2006.01)
*A61K 47/38* (2006.01)

(52) U.S. Cl.
CPC ............ *A61K 31/423* (2013.01); *A61K 47/26* (2013.01); *A61K 47/38* (2013.01)

(58) Field of Classification Search
CPC .................................................. A61K 31/423
See application file for complete search history.

(56) References Cited

U.S. PATENT DOCUMENTS

| 2005/0101636 A1 | 5/2005 | Yamazaki et al. |
| 2015/0196538 A1 | 7/2015 | Takizawa et al. |
| 2016/0136138 A1 | 5/2016 | Shibata et al. |

FOREIGN PATENT DOCUMENTS

| EP | 2 902 025 A1 | 8/2015 | |
| EP | 3 020 401 A1 | 5/2016 | |
| WO | WO 2005/023777 A1 | 3/2005 | |
| WO | WO 2014/050134 A1 | 4/2014 | |
| WO | WO 2015/005365 A1 | 1/2015 | |
| WO | 2902025 * | 8/2015 | ........... A61K 31/397 |
| WO | 3020401 * | 5/2016 | ........... A61K 31/423 |
| WO | WO2019-004449 | 1/2019 | |

OTHER PUBLICATIONS

Huang et al. Powder Tech. (2013) 246, pp. 379-384.*
Extended European Search Report dated Feb. 22, 2021 in European Patent Application No. 18825167.2, 7 pages.
Wan Huang, et al., "Using Spray-Dried Lactose Monohydrate in Wet Granulation Method for a Low-Dose Oral Formulation of a Paliperidone Derivative" Powder Technology, vol. 246, XP028691446, May 31, 2013, pp. 379-394.
International Search Report dated Aug. 21, 2018 in PCT/JP2018/024884 filed Jun. 29, 2018, 2 pages total.
"Report on the deliberation results of parmodia tablets 0.1 mg," Pharmaceutical Evaluation Division of Pharmaceutical Safety and Environmental Health Bureau, Ministry of Health, Labour and Welfare, Jul. 3, 2017, 84 pages total (with partial English translation).
Yamazaki et al., "Enantioselective Synthesis of the PPARα Agonist (R)-K-13675 via (S)-2-Hydroxybutyrolactone," Synthesis, No. 7, 2008, 7 pages total.
Fruchart, "Selective Peroxisome proliferator-activated receptorα modulators (SPPARMα): The next generation of peroxisome proliferator-activated receptor α-agonists," Cardiovascular Diabetology, vol. 12, No. 82, 2013, 8 pages total.
Japanese Office Action Issued in corresponding Japanese Patent Application No. 2016-126047 dated Jun. 7, 2022 (with machine translation).
Chinese Office Action dated Jun. 2, 2022 in corresponding Chinese Patent Application No. 201880043984.8 (with machine translation).
Wang Huang, et al., "Study on the impaction of pharmaceutical lactose properties on a low-dose tablet consent uniformity", Journal of Northeast Normal University, vol. 45, No. 3, Sep. 30, 2013, pp. 130-137 (including an English abstract on p. 137).

* cited by examiner

*Primary Examiner* — Paul V Ward
(74) *Attorney, Agent, or Firm* — Oblon, McClelland, Maier & Neustadt, L.L.P.

(57) ABSTRACT

Provided is a pharmaceutical composition containing pemafibrate, a salt thereof or a solvate thereof and having excellent homogeneity. The pharmaceutical composition is provided containing the following components (A) and (B): (A) pemafibrate, a salt thereof or a solvate thereof; and (B) a disaccharide species.

11 Claims, No Drawings

PHARMACEUTICAL COMPOSITION

FIELD OF THE INVENTION

The present invention relates to a pharmaceutical composition etc.

BACKGROUND OF THE INVENTION

It is known that pemafibrate (Chemical Name: (2R)-2-[3-([1,3-Benzoxazol-2-yl[3-(4-methoxyphenoxy)propyl]amino]methyl) phenoxy]butanoic acid) (International Nonproprietary Name: pemafibrate) represented by the following structural formula:

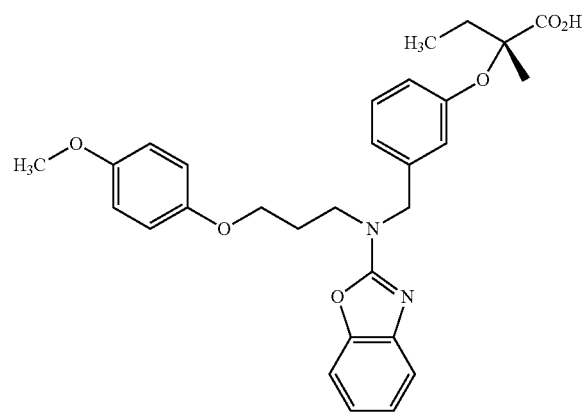 [SMILES: CC[C@@](C)(Oc1cccc(CN(CCCOc2ccc(OC)cc2)c2nc3ccccc3o2)c1)C(=O)O]

a salt thereof or a solvate thereof has excellent PPAR-α agonist activity, exhibits plasma triglyceride concentration reducing action, HDL cholesterol increasing action, etc., and is useful for prevention and treatment of dyslipidemia (hyperlipidemia) (Patent Document 1 and Non-Patent Documents 1 and 2), and useful for prevention and treatment of NAFLD (non-alcoholic fatty liver disease) (Patent Document 2).

Meanwhile, a compound useful as an active component for a pharmaceutical preparation is normally formulated as some pharmaceutical composition and supplied, and from the viewpoint of reliably exhibiting expected drug efficacy and avoiding unanticipated adverse side effects, it is very important that the pharmaceutical composition to be supplied maintains a certain level of quality without variations such as lot-to-lot variation.

PRIOR ART DOCUMENTS

Patent Documents

Patent Document 1: International Publication No. WO 2005/023777
Patent Document 2: International Publication No. WO 2015/005365

Non-Patent Documents

Non-Patent Document 1: Yukiyoshi Yamazaki, et al., Synthesis, 2008(7), 1017-1022.

Non-Patent Document 2: Fruchart J C., Cardiovasc Diabetol., 2013; 12: 82.

SUMMARY OF THE INVENTION

Problems to be Solved by the Invention

However, manufacturability of pharmaceutical compositions, such as homogeneity, significantly depends on the physical and chemical properties of components, but it is often impossible to predict such properties from the chemical structures of the components, and there are not a few cases where a problem becomes evident only when a pharmaceutical composition is actually produced. Thus, establishment of a technique for securing homogeneity of a pharmaceutical composition commonly requires considerable try and error.

Pemafibrate, a salt thereof or a solvate thereof has been only reported to exhibit the above-described pharmacological effects, and has heretofore not been specifically studied in terms of a pharmaceutical composition, and manufacturability such as homogeneity of the pharmaceutical composition has heretofore not been reported at all.

In these circumstances, for developing a pharmaceutical composition containing pemafibrate, a salt thereof or a solvate thereof, the present inventors have first actually produced the pharmaceutical composition. As a result, it was found that pharmaceutical compositions becomes different in content of pemafibrate, leading to development of problems with homogeneity (uniformity) of the content of pemafibrate. If pharmaceutical compositions significantly differ in content of pemafibrate, there may be variations in efficacy and safety among the pharmaceutical compositions.

Thus, an object of the present invention is to provide a pharmaceutical composition containing pemafibrate, a salt thereof or a solvate thereof, and having excellent homogeneity.

Means for Solving the Problems

In order to solve the problem with the content uniformity of pemafibrate, a salt thereof or a solvate thereof in a pharmaceutical composition, the present inventors have further extensively conducted studies, and found that by further incorporating disaccharide species typified by lactose (hereinafter, sometimes referred to simply as "component (B)") in the pharmaceutical composition comprising pemafibrate, a salt thereof or a solvate thereof (hereinafter, sometimes referred to simply as "component (A)"), the content uniformity of pemafibrate in the pharmaceutical composition is improved. The present invention has been accomplished on the basis of this finding.

Accordingly, the present invention provides a pharmaceutical composition containing the following components (A) and (B):
(A) pemafibrate, a salt thereof or a solvate thereof; and
(B) a disaccharide species.

The present invention also provides a method for improving the content uniformity of pemafibrate, a salt thereof or a solvate thereof in a pharmaceutical composition, the method including the step of incorporating disaccharide species in the pharmaceutical composition containing pemafibrate, salt thereof or a solvate thereof.

Effects of the Invention

According to the present invention, it is possible to provide a pharmaceutical composition having improved content uniformity of pemafibrate in the pharmaceutical composition and having excellent homogeneity.

DETAILED DESCRIPTION OF THE INVENTION

Pemafibrate, Salt Thereof or Solvate Thereof (Component (A))

Herein, "pemafibrate, a salt thereof or a solvate thereof" includes pemafibrate (Chemical Name: (2R)-2-[3-([1,3-Benzoxazol-2-yl[3-(4-methoxyphenoxy) propyl]amino] methyl)phenoxy]butanoic acid) (International Nonproprietary Name: pemafibrate) itself, a pharmaceutically acceptable salt of pemafibrate and a solvate of pemafibrate or a pharmaceutically acceptable salt thereof with water, alcohol (for example ethanol) or the like. The pharmaceutically acceptable salt is not particularly limited, and examples thereof include acid addition salts and base addition salts. Specific examples of the acid addition salts include acid addition salts with inorganic acids, such as hydrochlorides, hydrobromides, hydroiodides, sulfate salts, nitrate salts and phosphate salts; and acid addition salts with organic acids, such as benzoate salts, methanesulfonate salts, ethanesulfonate salts, benzenesulfonate salts, p-toluenesulfonate salts, maleate salts, fumarate salts, tartrate salts, citrate salts and acetate salts. Specific examples of the base addition salts include metal salts such as sodium salts, potassium salts, lithium salts, calcium salts and magnesium salts; salts with amines such as ammonia, trimethylamine, triethylamine, pyridine, collidine and lutidine; and base addition salts with organic bases such as lysine, arginine, cinchonine and cinchonidine.

The shape, the size and the like of pemafibrate, a salt thereof or a solvate thereof are not particularly limited, and when the average particle diameter of primary particles is measured in accordance with The Japanese Pharmacopoeia, 17th Edition, Laser Diffraction Measurement of Particle Size, d50 and d90 values are preferably as follows.

d50: preferably 100 µm or less, more preferably 50 µm or less, still more preferably 20 µm or less, particularly preferably 1 to 20 µm.

d90: preferably 200 µm or less, more preferably 135 µm or less, still more preferably 80 µm or less, particularly preferably 1 to 80 µm.

Pemafibrate, a salt thereof or a solvate thereof is a known compound, and can be produced through a method as disclosed in Patent Document 1, Non-Patent Document 1 or U.S. Pat. No. 7,109,226, for example. In the present invention, a pemafibrate crystal which can be produced through the method described in Non-Patent Document 1 (preferably a crystal showing a melting point of 95 to 101° C., particularly preferably 97 to 100° C. in measurement performed in accordance with The Japanese Pharmacopoeia, 17th Edition, Melting Point Determination Method 1) is preferably used. The disclosures of the documents are incorporated herein by reference.

The content of pemafibrate, a salt thereof or a solvate thereof in the pharmaceutical composition is not particularly limited, and can be determined in appropriate consideration of the target disease, the type of preparation, the sex, age and symptoms of a patient in need of the composition, and the like. For example, the content can be set so that the daily dose of pemafibrate, a salt thereof or a solvate thereof may be 0.05 to 0.8 mg, more preferably 0.075 to 0.6 mg, particularly preferably 0.1 to 0.4 mg, in terms of a free form of pemafibrate.

The content of pemafibrate, a salt thereof or a solvate thereof in the pharmaceutical composition is preferably 0.01 to 5 mass %, more preferably 0.025 to 1 mass %, particularly preferably 0.05 to 0.5 mass %, in terms of a free form of pemafibrate, with respect to the total mass of the pharmaceutical composition. According to the present invention, even if pemafibrate, a salt thereof or a solvate thereof has such a small content, a good content uniformity can be obtained.

Disaccharide Species (Component (B))

Herein, the "disaccharide species" means one or more selected from the group consisting of a disaccharide itself; a disaccharide in which all or some of hydroxy groups are substituted with halogen atoms such as chlorine atoms; and a solvate thereof. Here, the solvate is not particularly limited, and specific examples thereof include hydrates. The type of monosaccharide forming the disaccharide is not particularly limited, and examples thereof include pentoses such as arabinose and xylose; and hexoses such as glucose, galactose, fructose, mannose, altrose and rhamnose.

Specific examples of the disaccharide species include sucrose (cane sugar) lactulose, lactose (milk sugar), maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, rutinulose, vicianose, xylobiose, primevelose and sucralose, and these disaccharides may be used singly, or in combinations of two or more thereof.

From the viewpoint of improvement of content uniformity, the disaccharide species is preferably one or more selected from the group consisting of sucrose, lactose, maltose, trehalose, palatinose, sucralose and a solvate thereof, more preferably one or more selected from the group consisting of sucrose, lactose, trehalose, sucralose and a hydrate thereof, still more preferably one or more selected from the group consisting of lactose and a hydrate thereof, particularly preferably one or more selected from the group consisting of a lactose/microcrystalline cellulose spherical grain, a lactose monohydrate, a lactose granularized product and an anhydrous lactose. From the viewpoint of ease of production of a pharmaceutical composition (particularly a solid preparation), the disaccharide species is preferably solid at normal temperature (any temperature in the range of 15 to 25° C.)

Each of these disaccharide species is a known component. The disaccharide species may be produced through a known method, or commercially available products may be used. Examples of the commercially available products include NONPAREIL-105 (Freund Corporation), Lactose monohydrate (San-Ei Gen F. F. I., Inc.), Lactose G (Freund Corporation), Lactopress anhydrous (CBC Co., Ltd.), Nishoku Crystalline Maltose (Nihon Shokuhin Kako Co., Ltd.), Trehalose P (Asahi Kasei Corporation), Sucralose (San-Ei Gen F. F. I., Inc.) and Pharmatose 200M (DFE pharma).

The content of the disaccharide species in the pharmaceutical composition is not particularly limited, and can be determined in appropriate consideration of the type of preparation, the sex, age and symptoms of a patient in need of the composition, and the like, but from the viewpoint of improvement of content uniformity, the total amount at the disaccharide species with respect to the total mass of the pharmaceutical composition is preferably 1 to 99 mass %, more preferably 3 to 95 mass %, still more preferably 5 to 90 mass %, particularly preferably 7 to 85 mass %.

When one or more selected from the group consisting of lactose and a hydrate thereof are used as the disaccharide species, the content thereof with respect to the total mass of the pharmaceutical composition is preferably 2 to 98 mass %, more preferably 4 to 93 mass %, particularly preferably 8 to 80 mass %, from the viewpoint of improvement of content uniformity.

The mass ratio between the content of pemafibrate, a salt thereof or a solvate thereof and the content of the disaccharide species in the pharmaceutical composition is not particularly limited, and from the viewpoint of improvement of content uniformity, the total content of the disaccharide species with respect to 1 part by mass of a free form of pemafibrate is preferably 10 to 1,750 parts by mass, more preferably 50 to 1,500 parts by mass, still more preferably 80 to 1,200 parts by mass, particularly preferably 100 to 900 parts by mass.

When one or more selected from the group consisting of lactose and a hydrate thereof are used as the disaccharide species, the mass ratio between the content of pemafibrate, a salt thereof or a solvate thereof and the content of one or more selected from the group consisting of lactose and a hydrate thereof in the pharmaceutical composition is not particularly limited, and from the viewpoint of improvement of content uniformity, the total content of one or more selected from the group consisting of lactose and a hydrate thereof with respect to 1 part by mass of a free form of pemafibrate is preferably 30 to 1,150 parts by mass, more preferably 50 to 1,050 parts by mass, still more preferably 70 to 950 parts by mass, particularly preferably 120 to 850 parts by mass.

Cellulose (Component (C))

The pharmaceutical composition of the present invention preferably contains cellulose in addition to component (A) and component (B). By incorporating the disaccharide species and cellulose in combination, the content uniformity of pemafibrate becomes more excellent.

Herein, the "cellulose" means one or more selected from the group consisting of cellulose and a salt thereof. In the cellulose, the salt is not particularly limited, and specific examples thereof include alkali metal salts such as sodium salts and potassium salts; and salts with metals of Group 2 elements, such as calcium salts and magnesium salts. The average degree of polymerization, the form (crystal form) and the like of the cellulose are not particularly limited, and the average degree of polymerization is preferably 50 to 10,000. Here, the average degree of polymerization can be determined by conducting a test in accordance with Identification (3) described in The Japanese Pharmacopoeia, 17th Edition, "Microcrystalline Cellulose".

Specific examples of the cellulose include crystalline cellulose, crystalline cellulose (fine particles), crystalline cellulose (grain), powdered cellulose and powdered cellulose (average degree of polymerization: 800 to 1,100), and these celluloses may be used singly, or in combinations of two or more thereof. The crystalline cellulose and the like are the crystalline cellulose and the like described in Japanese Pharmaceutical Excipients Directory 2016 (issued by Yakuli Nippo, Limited).

Each of these celluloses is a known component. The celluloses may be produced through a known method, or commercially available products may be used. Examples of the commercially available products include CEOLUS PH-101. (Asahi Kasei Corporation), CELPHERE (San-Bi Gen F. F. I., Inc.) and ARBOCEL (Kimura Sangyo Co., Ltd.)

The content of the cellulose in the pharmaceutical composition is not particularly limited, and can be determined in appropriate consideration of the type of preparation, the sex, age and symptoms of a patient in need of the composition, and the like, but from the viewpoint of improvement of content uniformity, the total amount of the cellulose with respect to the total mass of the pharmaceutical composition is preferably 1 to 40 mass %, more preferably 3 to 35 mass %, still more preferably 5 to 30 mass %, particularly preferably 8 to 25 mass %.

The mass ratio between the content of pemafibrate, a salt thereof or a solvate thereof and the content of the cellulose in the pharmaceutical composition is not particularly limited, and from the viewpoint of improvement of content uniformity, the total content of the cellulose with respect to 1 part mass of a free form of pemafibrate is preferably 5 to 5,000 parts by mass, more preferably 30 to 3,500 parts by mass, particularly preferably 60 to 2,000 parts by mass.

Herein, the dosage form of the "pharmaceutical composition" is not particularly limited, may be a solid, semisolid or liquid preparation, and can be selected according to the use purpose of the pharmaceutical composition. Examples of the dosage form of the pharmaceutical composition include dosage forms described in The Japanese Pharmacopoeia, 17th Edition, General Rules for Preparations. Specific examples of the peroral dosage form include solid preparations such as tablets (e.g. normal tablets, orally disintegrating tablets, chewable tablets, effervescent tablets, dispersion tablets and soluble tablets), capsules, granules (e.g. effervescent granules), powders and pills; semisolid preparations such as peroral jellies; liquid preparations such as peroral liquids (e.g. elixirs, suspensions, emulsions and lemonades). Examples of the parenteral dosage form include injections, inhalations, eye drops, ear drops, nasal drops, suppositories, solid external preparations, liquid external preparations, sprays, ointments, creams, gels and patches.

The pharmaceutical composition is preferably a solid preparation from the viewpoint of ease of administration and ease of production. In particular, when the pharmaceutical composition is a solid preparation, production is very easy, but since in general, a solid preparation is produced basically with solid components used in a large amount at normal temperature (any temperature in the range of 15 to 25° C.), components are apt to be unevenly mixed and dispersed, so that deterioration in content uniformity is apt to be particularly problematic. On the other hand, the present invention exhibits the following excellent advantage: even a solid preparation has good content uniformity.

The solid preparation is preferably a peroral solid preparation, more preferably a tablet, a capsule, a granule, a powder or a pill, particularly preferably a tablet. In addition, the solid preparation is preferably a solid preparation containing a mixture comprising component (A) and component (B), more preferably a solid preparation containing a mixture comprising components (A) to (C).

In addition to the above-described components, pharmaceutically acceptable carriers (additives for pharmaceutical preparation) may be added to the pharmaceutical composition of the present invention depending on its dosage form. Examples of the additives for pharmaceutical preparation include, but are not limited to, diluents, disintegrants, binders, lubricants, plasticizers, film formers, powders, poorly water-soluble polymer substances, antioxidants, flavors and sweetening agents. As specific examples of these additives for pharmaceutical preparation, those described in Japanese Pharmaceutical Excipients Directory 2016 (issued by Yakuji Nippo, Limited), Handbook of Pharmaceutical Excipients, Seventh Edition (issued by Pharmaceutical Press), etc. may be used.

Specific examples of the diluents include: inorganic diluents such as aluminum silicate, anhydrous sodium sulfate, sodium chloride, light anhydrous silicic acid, heavy anhydrous silicic acid, calcium sulfate, calcium monohydrogen phosphate, dibasic sodium phosphate, monobasic potassium phosphate, monobasic calcium phosphate and sodium dihydrogen phosphate; and organic diluents such as starch (wheat starch, rice starch, cornstarch, partially pregelatinized starch, etc.), fructose, caramel, agar, xylitol, paraffin, glucose, pullulan, polyoxyethylene hydrogenated castor oil, maltitol, erythritol, sorbitol, mannitol, lactitol, aminoalkyl methacrylate copolymers E, polyvinylacetal diethylaminoacetate and calcium citrate. These diluents may be used singly, or in combinations of two or more thereof.

Among these diluents, light anhydrous silicic acid and mannitol are preferable.

Specific examples of the disintegrants include superdisintegrants such as carboxymethyl starch sodium, croscarmellose sodium and crospovidone, carmellose, carmellose calcium, starch, sucrose fatty acid ester, gelatin, dextrin, dehydroacetic acid and salts thereof, povidone and polyoxyethylene hydrogenated castor oil 60. These disintegrants may be used singly, or in combinations of two or more thereof.

Among these disintegrants, carboxymethyl starch sodium and croscarmellose sodium are preferable.

Specific examples of the binders include oils and fats such as tallow hydrogenated oil, hydrogenated oil, hydrogenated vegetable oil, soybean hydrogenated oil, carnauba wax, white beeswax, yellow beeswax and Japan wax, methylcellulose, hydroxypropylcellulose, hypromellose, carmellose sodium, starch (wheat starch, rice starch, corn starch, partially pregelatinized starch, etc.), dextrin, pullulan, acacia, agar, gelatin, tragacanth, sodium alginate, povidone, polyvinyl alcohol, aminoalkyl methacrylate copolymer E and polyvinylacetal diethylaminoacetate. These binders may be used singly, or in combinations of two or more thereof.

Among these binders, carnauba wax, hydroxypropylcellulose, hypromellose, povidone and aminoalkyl methacrylate copolymer E are preferable.

Specific examples of the lubricants include calcium stearate, magnesium stearate, sodium stearyl fumarate and sucrose fatty acid ester. Theses lubricants may be used singly, or in combinations of two or more thereof.

Among these lubricants, calcium stearate, magnesium stearate and sodium stearyl fumarate are preferable.

Specific examples of the plasticizers include triethyl citrate, glycerin, sesame oil, sorbitol, castor oil and polysorbate 80 (polyoxyethylene(20)sorbitan oleate). These plasticizers may be used singly, or in combinations of two or more thereof.

Among these plasticizers, triethyl citrate, glycerin and sorbitol are preferable.

Specific examples of the film formers include alkylcelluloses such as methylcellulose and ethylcellulose; alginic acid or salts thereof such as sodium alginate; carrageenan; carboxyalkylcelluloses such as carboxymethylcellulose sodium, carboxymethylcellulose calcium, carboxymethylcellulose potassium, carboxymethylcellulose and carboxymethylethylcellulose; xanthan gum; hydroxyalkylcelluloses such as hydroxymethylcellulose, hydroxyethylcellulose, hydroxypropylcellulose, hypromellose (hydroxypropylmethylcellulose); hydroxyalkylcellulose phthalate such as hydroxypropylmethylcellulose phthalate; pullulan; polyvinyl acetate; polyvinyl acetate phthalate; and polyvinylpyrrolidone. These film formers may be used singly, or in combinations of two or more thereof.

Among these film formers, alkylcelluloses and hydroxyalkylcelluloses are preferable.

Specific examples of the powders include organic and inorganic powders such as powders of talc, titanium oxide, yellow ferric oxide, red ferric oxide and legal color pigments. These powders may be used singly, or in combinations of two or more thereof.

Among these powders, titanium oxide, yellow ferric oxide, red ferric oxide and legal color pigments are preferable.

Specific examples of the poorly water-soluble polymer substances include carboxyvinyl polymers and aminoalkyl methacrylate copolymers. These substances may be used singly, or in combinations of two or more thereof.

Specific examples of the antioxidants include ascorbic acid, sodium hydrogen sulfite, sodium sulfite, sodium edetate, erythorbic acid, tocopherol acetate, dibutylhydroxytoluene, natural vitamin E, tocopherol and butylhydroxyanisole. These antioxidants may be used singly, or in combinations of two or more thereof.

Specific examples of the flavors include terpenes such as limonene, pinene, camphene, cymene, cineole, citronellol, geraniol, nerol, linalool, menthol, terpineol, rhodinol, borneol, isoborneol, menthone, camphor, eugenol and cinnzeylanol; terpene-containing essential oils such as bitter orange oil, orange oil, peppermint oil, camphor white oil, eucalyptus oil, turpentine oil, lemon oil, ginger oil, clove oil, cinnamon oil, lavender oil, fennel oil, chamomile oil, fermented soybean oil and spearmint oil; and acidifiers such as ascorbic acid, tartaric acid, citric acid, malic acid and salts thereof. These flavors may be used singly, or in combinations of two or more thereof.

Examples of the sweetening agents include aspartame, stevia, glycyrrhizic acid, thaumatin, acesulfame potassium, saccharin and saccharin sodium, and these sweetening agents may be used singly, or in combinations of two or more thereof.

The pharmaceutical composition of the present invention preferably contains one or more selected from the group consisting of croscarmellose sodium, magnesium stearate, titanium oxide, triethyl citrate, hypromellose, hydroxypropylcellulose, light anhydrous silicic acid and carnauba wax, among the above-mentioned pharmaceutically acceptable carriers.

The pharmaceutical composition of the present invention can be produced through a known method depending on its dosage form.

For example, the pharmaceutical composition, when it is a solid preparation, can be produced through appropriate combination of unit operations such as grinding, mixing, granulation, drying, grain size adjustment, classification, filling, pelletizing and coating. However, the method for producing the same preferably involves a step of mixing component (A) and component (A), more preferably involves a step of mixing components (A) to (C).

More specifically, for example, when the dosage form of the pharmaceutical composition is a granular preparation such as a granule, a powder or a pill, component (A) and component (B) are mixed with component (C) and additives for pharmaceutical preparation such as diluents, binders, disintegrants and lubricants in accordance with needs, the mixture is then granulated through a known granulation method such as extrusion granulation, tumbling granulation, agitation granulation, fluidized bed granulation, spray granulation, melt granulation or crushing granulation to obtain a granulated product, and the granulated product is subjected to classification, grain size adjustment and the like in accordance with needs, whereby the pharmaceutical composition can be produced. The obtained granulated product can be coated through a known method with a coating agent etc.

When the dosage form of the pharmaceutical composition is a tablet, component (A) and component (B) are mixed with component (C) and additives for pharmaceutical preparation such as diluents, binders, disintegrants and lubricants in accordance with needs to obtain a mixture, and the mixture is directly compressed (pelletized) (through a direct powder compression method), or compressed (pelletized) (through a semidry grain compression method, dry granule compression method, wet grain compression method or the like) after the above-described granulated product is subjected to classification, grain size adjustment and the like, whereby the pharmaceutical composition can be produced. The obtained compressed product (tablet) can be coated through a known method with a coating agent etc.

When the dosage form of the pharmaceutical composition is a capsule, the granulated product or compressed product may be capsulated.

The disease to which the pharmaceutical composition of the present invention is applied is not limited, and the pharmaceutical composition can be widely used for prevention or treatment of diseases against which administration of pemafibrate is known or expected to be effective.

For example, pemafibrate, a salt thereof or a solvate thereof has excellent PPAR-α agonist activity, and exhibits plasma triglyceride concentration reducing action, HDL cholesterol increasing action, etc. Therefore, the pharmaceutical composition of the present invention can be used preferably as an agent for prevention and/or treatment of dyslipidemia (hyperlipidemia, more specifically, for example primary hyperlipidemia and secondary hyperlipidemia), further preferably as an agent for prevention and/or treatment of hypertriglyceridemia, etc.

In addition, pemafibrate, a salt thereof or a solvate thereof is useful for prevention or treatment of NAFLD (non-alcoholic fatty liver disease). Therefore, the pharmaceutical composition of the present invention can also be used as an agent for prevention and/or treatment of NAFLD (more preferably NASH (non-alcoholic steatohepatitis)), etc.

Further, pemafibrate, a salt thereof or a solvate thereof may be used as an agent for treatment of primary biliary cirrhosis.

The administration route of the pharmaceutical composition is not particularly limited, and can be determined in appropriate consideration of the target disease, the type of preparation, the sex, age, symptoms of a patient in need of the composition, and the like, but peroral administration is preferable from the viewpoint of ease of administration. The daily dose of the pharmaceutical composition can be taken as a single dose, or can be divided into 2 to 4 daily administrations, and taken before each meal, between meals, after each meal, before bedtime, or the like.

For example, the following aspects are disclosed herein and should not be construed as limiting the present invention.

[1-1] A pharmaceutical composition comprising the following components (A) and (B):
(A) pemafibrate, a salt thereof or a solvate thereof; and
(B) a disaccharide species.

[1-2] The pharmaceutical composition according to [1-1], wherein the component (B) is one or more selected from the group consisting of sucrose (cane sugar), lactulose, lactose (milk sugar), maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, rutinulose, vicianose, xylobiose, primevelose, sucralose and a solvate thereof.

[1-3] The pharmaceutical composition according to [1-1], wherein the component (B) is one or more selected from the group consisting of sucrose, lactose, maltose, trehalose, palatinose, sucralose and a solvate thereof.

[1-4] The pharmaceutical composition according to [1-1], wherein the component (B) is one or more selected from the group consisting of sucrose, lactose, trehalose, sucralose and a hydrate thereof.

[1-5] The pharmaceutical composition according to [1-1], wherein the component (B) is one or more selected from the group consisting of lactose and a hydrate thereof.

[1-6] The pharmaceutical composition according to any one of [1-1] to [1-5], further comprising a component (C):
(C) cellulose.

[1-7] The pharmaceutical composition according to any one of [1-1] to [1-6], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[1-8] The pharmaceutical composition according to any one of [1-1] to [1-7], wherein the pharmaceutical composition is a solid preparation.

[1-9] The pharmaceutical composition according to any one of [1-1] to [1-8], wherein a dosage form thereof is a tablet, a capsule, a granule, a powder or a pill.

[2-1] A method for improving content uniformity of pemafibrate, a salt thereof or a solvate thereof in a pharmaceutical composition, the method comprising the step of incorporating the following component (B):
(B) a disaccharide species
in a pharmaceutical composition comprising
(A) pemafibrate, a salt thereof or a solvate thereof.

[2-2] The method according to [2-1], wherein the component (B) is one or more selected from the group consisting of sucrose (cane sugar), lactulose, lactose (milk sugar), maltose, trehalose, cellobiose, kojibiose, nigerose, isomaltose, isotrehalose, neotrehalose, sophorose, laminaribiose, gentiobiose, turanose, maltulose, palatinose, gentiobiulose, mannobiose, melibiose, melibiulose, neolactose, galactosucrose, scillabiose, rutinose, rutinulose, vicianose, xylobiose, primevelose, sucralose and a solvate thereof.

[2-3] The method according to [2-1], wherein the component (B) is one or more selected from the group consisting of sucrose, lactose, maltose, trehalose, palatinose, sucralose and a solvate thereof.

[2-4] The method according to [2-1], wherein the component (B) is one or more selected from the group consisting of sucrose, lactose, trehalose, sucralose and a hydrate thereof.

[2-5] The method according to [2-1], wherein the component (B) is one or more selected from the group consisting of lactose and a hydrate thereof.

[2-6] The method according to any one of [2-1] to [2-5], further comprising the step of incorporating a component (C):
(C) cellulose.

[2-7] The method according to any one of [2-1] to [2-6], wherein the pharmaceutical composition is an agent for prevention and/or treatment of a disease selected from dyslipidemia (hyperlipidemia, more specifically, for example primary hyperlipidemia and secondary hyperlipidemia), NAFLD (more preferably NASH (non-alcoholic steatohepatitis)) and primary biliary cirrhosis.

[2-8] The method according to any one of [2-1] to [2-7], wherein the pharmaceutical composition is a solid preparation.

[2-9] The method according to any one of [2-1] to [2-8], wherein a dosage form of the pharmaceutical composition is a tablet, a capsule, a granule, a powder or a pill.

EXAMPLES

The present invention will next be described in detail by way of Examples, which should not be construed as limiting the invention thereto.

In Test Examples below, measurement was performed through HPLC using an ODS column as a column and an ultraviolet spectrophotometer as a detector.

For pemafibrate used in Test Examples below, the average particle diameters of primary particles were measured in accordance with The Japanese Pharmacopoeia, 17th Edition, Laser Diffraction Measurement of Particle Size, and the results showed that the d50 value was 100 µm or less, and the d90 value was 200 µm or less.

Test Example 1

Content Uniformity Evaluation Test

The following test was conducted for evaluating the uniformity of the content of pemafibrate in a pharmaceutical composition.

The tablets were produced using the components shown in Table 1 in such a manner that the amounts (mg) of the components per tablet were as shown in Table 1. Specific procedures will be described below.

Example 1

Pemafibrate, lactose monohydrate, croscarmellose sodium and hydroxypropylcellulose were mixed for 5 minutes, purified water was then added, and the mixture was kneaded for 3 minutes, granulated, dried, and then sized to obtain a granulation product. Magnesium stearate was mixed with the obtained granulation product, and the mixture was then compressed to produce 10,000 tablets each having a weight of 120 mg.

Example 2

10,000 tablets each having a weight of 120 mg were produced through the same method as in Example 1 except that the lactose monohydrate was partially replaced by microcrystalline cellulose.

Comparative Example 1

10,000 tablets each having a weight of 120 mg were produced through the same method as in Example 1 except that the lactose monohydrate was all replaced by microcrystalline cellulose.

From the tablets obtained in Examples and Comparative Example, ten tablets were randomly picked up, and the content of pemafibrate in each tablet was measured through the following method.

One tablet was put in water to crush the tablet, and acetonitrile was then added to obtain a sample solution. The obtained sample solution was analyzed with a HPLC apparatus to measure the pemafibrate-derived peak area. By comparing the pemafibrate-derived peak area for the obtained sample solution to the peak area for a standard solution of pemafibrate with a known concentration, the pemafibrate content per tablet was measured.

From the thus-obtained measured value of the pemafibrate content per tablet, a relative standard deviation (RSD) (%) of the pemafibrate content in the tablet was calculated in accordance with The Japanese Pharmacopoeia, 17th Edition, Content Uniformity Test, and used as an index of variation (degree of uniformity) of the pemafibrate content in the tablet.

Table 1 shows the results.

TABLE 1

| | Amount blended (mg) (per tablet) | | |
|---|---|---|---|
| Components | Example 1 | Example 2 | Comparative Example 1 |
| Pemafibrate | 0.1 | 0.1 | 0.1 |
| Lactose monohydrate (Pharmatose 200M: DFE Pharma) | 110.3 | 98.3 | — |
| Microcrystalline cellulose (CEOLUS PH-102: Asahi Kasei Corporation) | — | 12.0 | 110.3 |
| Croscarmellose sodium (KICCOLATE ND-2HS: Nichirin Chemical Industries, Ltd.) | Balance | Balance | Balance |
| Hydroxypropylcellulose (HPC-L: Nippon Soda Co., Ltd.) | | | |
| Magnesium stearate | | | |
| Total | 120 | 120 | 120 |
| Relative standard deviation (RSD) (%) | 1.6 | 1.4 | 4.0 |

The amount blended of pemafibrate in the table is a value calculated from the amount added.

As is apparent from the results shown in Table 1, tablets (Examples 1 and 2) containing lactose monohydrate as the disaccharide species all had a small relative standard deviation as compared with tablets of Comparative Example 1 not containing the disaccharide species, and good uniformity of the content of pemafibrate per tablet. In particular, the tablets of Example 2 containing crystalline cellulose in addition to lactose monohydrate had a smaller relative standard deviation and more excellent uniformity of the content of pemafibrate per tablet.

The above test results reveal that the content uniformity of pemafibrate in the pharmaceutical composition is improved by incorporating disaccharide species in a pharmaceutical composition containing pemafibrate, a salt thereof or a solvate thereof.

Production Examples 1 to 3

Tablets containing the components in the amounts (mg) thereof per tablet shown in Table 2 are conventionally produced through a wet grain compression method.

TABLE 2

| | Production Example 1 | Production Example 2 | Production Example 3 |
|---|---|---|---|
| Pemafibrate | 0.1 | 0.4 | 0.1 |
| Corn starch | q.s. | q.s. | q.s. |
| Hydroxypropylmethylcellulose | 10 | 20 | 5 |
| Polyvinylpyrrolidone | 5 | 5 | 5 |

TABLE 2-continued

|  | Production Example 1 | Production Example 2 | Production Example 3 |
|---|---|---|---|
| Magnesium stearate | 1 | 1 | 1 |
| Lactose monohydrate | 20 | | |
| Trehalose hydrate | | 30 | |
| Sucralose | | | 50 |
| Microcrystalline cellulose | | | |
| Total | 100 mg | 100 mg | 100 mg |

The amount blended of pemafibrate in the table is a value calculated from the amount added.

Production Examples 4 to 6

Tablets containing the components in the amounts (mg) thereof per tablet shown in Table 3 are conventionally produced through a direct powder compression method.

TABLE 3

|  | Production Example 4 | Production Example 5 | Production Example 6 |
|---|---|---|---|
| Pemafibrate | 0.1 | 0.4 | 0.1 |
| Corn starch | q.s. | q.s. | q.s. |
| Magnesium stearate | 1 | 1 | 1 |
| Lactose monohydrate | 60 | | 5 |
| Trehalose hydrate | | 40 | 5 |
| Sucralose | | | 5 |
| Microcrystalline cellulose | 5 | 15 | 25 |
| Total | 100 mg | 100 mg | 100 mg |

The amount blended of pemafibrate in the table is a value calculated from the amount added.

Industrial Applicability

The present invention enables provision of a pharmaceutical composition having excellent homogeneity and containing pemafibrate which exhibits plasma triglyceride concentration reducing action, HDL cholesterol increasing action, etc. The pharmaceutical composition can be used in, for example, pharmaceutical preparation industries.

The invention claimed is:

1. A solid pharmaceutical composition comprising the following components (A) and (B):
   (A) pemafibrate, a salt thereof or a solvate thereof; and
   (B) from at least 10 to 1750 part by mass of at least one of lactose or a lactose hydrate per 1 part by mass of the free form of pemafibrate.

2. The pharmaceutical composition of claim 1, further comprising a component (C):
   (C) cellulose.

3. The pharmaceutical composition of claim 1, wherein the pharmaceutical composition is a solid preparation.

4. The pharmaceutical composition of claim 1, wherein a dosage form thereof is a tablet, a capsule, a granule, a powder or a pill.

5. A method for improving content uniformity of pemafibrate, a salt thereof or a solvate thereof in a pharmaceutical composition, the method comprising the step of incorporating in a solid pharmaceutical composition comprising pemafibrate, a salt thereof or a solvate thereof from at least 10 to 1750 part by mass of at least one of lactose or a lactose hydrate per 1 part by mass of the free form of pemafibrate.

6. The composition of claim 1 wherein the composition comprises from at least 100 to 900 part by mass of at least one of lactose or a lactose hydrate per 1 part by mass of the free form of pemafibrate.

7. The composition of claim 1 wherein the composition comprises from at least 80 to 1200 part by mass of at least one of lactose or a lactose hydrate per 1 part by mass of the free form of pemafibrate.

8. The composition of claim 1 wherein the composition comprises from at least 50 to 1500 part by mass of at least one of lactose or a lactose hydrate per 1 part by mass of the free form of pemafibrate.

9. The method of claim 5 wherein from at least 100 to 900 part by mass of at least one of lactose or a lactose hydrate per 1 part by mass of the free form of pemafibrate is incorporated into the solid pharmaceutical composition.

10. The method of claim 5 wherein from at least 80 to 1200 part by mass of at least one of lactose or a lactose hydrate per 1 part by mass of the free form of pemafibrate is incorporated into the solid pharmaceutical composition.

11. The method of claim 5 wherein the from at least 50 to 1500 part by mass of at least one of lactose or a lactose hydrate per 1 part by mass of the free form of pemafibrate is incorporated into the solid pharmaceutical composition.

* * * * *